US00PP18131P2

(12) United States Plant Patent
Woolmore

(10) Patent No.: US PP18,131 P2
(45) Date of Patent: Oct. 16, 2007

(54) ***PHORMIUM* PLANT NAMED 'TWISTED SISTER'**

(50) Latin Name: *Phormium tenax*
Varietal Denomination: TWISTED SISTER

(76) Inventor: Malcolm Woolmore, Po Box 81-022, Whenuapia, Auckland (NZ)

( * ) Notice: Subject to any disclaimer, the term of this patent is extended or adjusted under 35 U.S.C. 154(b) by 16 days.

(21) Appl. No.: 11/351,585

(22) Filed: Feb. 9, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para

(57) ABSTRACT

A new cultivar of *Phormium* plant named 'TWISTED SISTER' that is characterized by upright clumping habit, small overall size, and twisted leaves that are grey-green in color, with a pronounced orange-brown margin. In combination these traits set 'TWISTED SISTER' apart from all other existing varieties of *Phormium* known to the inventor.

2 Drawing Sheets

Genus: *Phormium*. Species: *tenax*.
Denomination: 'TWISTED SISTER'.

BACKGROUND OF THE INVENTION

The present invention relates to a new and distinct variety of New Zealand flax grown for use in the landscape, or for use as a container plant. The new cultivar is known botanically as *Phormium tenax* and will be referred to hereinafter by the cultivar name 'TWISTED SISTER'.

The new *Phormium* cultivar named 'TWISTED SISTER' is a naturally occurring whole plant mutation that was discovered by the inventor in a cultivated area of Auckland, New Zealand. The parent of 'TWISTED SISTER' is one individual *Phormium tenax* (unpatented) that was growing within a commercial crop of *Phormium tenax*. The inventor selected 'TWISTED SISTER' in 2000 based on the perceived uniqueness of plant habit, leaf form, leaf color and leaf margin. The inventor then isolated 'TWISTED SISTER' for continued observation, and grew it on to maturity.

'TWISTED SISTER' exhibits upright clumping habit, low to moderate vigor, small overall size, and short broad twisted leaves that are grey-green in color, with a pronounced orange-brown margin. The plant 'TWISTED SISTER' is fan-shaped with stiff leaves that are folded lengthwise, with leaf bases overlapping in a single row. Cultural requirements include full sun to part shade, occasional to regular water, and well-draining loam soil. There is no resistance to pests or disease known to the inventor, and 'TWISTED SISTER' has produced no flowers to date.

The new *Phormium* cultivar 'TWISTED SISTER' is distinguishable from the parent by overall plant size, leaf form, leaf length, leaf color, and leaf margin. *Phormium tenax* exhibits large overall plant size, straight nine-foot-long leaves, and bronze-green foliage color. The closest comparison plants to 'TWISTED SISTER' are *Phormium* 'Surfer' (unpatented) and *Phormium* 'Jack Sprat' (unpatented). 'TWISTED SISTER' is distinguishable from 'Surfer' by vigor, plant habit, and leaf width. The comparison plant 'Surfer' is vigorously clumping and exhibits fine, narrow leaves. 'TWISTED SISTER' is distinguishable from 'Jack Sprat' by vigor, plant habit and foliage color. The foliage of 'Jack Sprat' is bronze in color, and the plant habit is vigorously clumping. Neither the parent nor the comparison plants exhibit any pronounced leaf margin.

'TWISTED SISTER' was first asexually propagated in 2001, by the inventor in Auckland, New Zealand. The method of asexual propagation used was tissue culture. The inventor has determined that the characteristics of the new *Phormium* cultivar named 'TWISTED SISTER' are fixed, stable and reproduce true to type in successive generations of asexual reproduction.

SUMMARY OF THE INVENTION

The following traits have been repeatedly observed and represent the distinguishing characteristics of the new *Phormium* variety named 'TWISTED SISTER'. In combination these traits set 'TWISTED SISTER' apart from all other *Phormium* known to the inventor. 'TWISTED SISTER' has not been tested under all possible conditions and phenotypic differences may be observed with variations in environmental, climatic and cultural conditions, however, without any variance in genotype.

1. *Phormium tenax* 'TWISTED SISTER' exhibits upright clumping habit.
2. *Phormium tenax* 'TWISTED SISTER' exhibits low to moderate vigor and small overall size.
3. *Phormium tenax* 'TWISTED SISTER' exhibits short broad leaves that are grey-green with pronounced orange-brown margins.
4. *Phormium tenax* 'TWISTED SISTER' is a fan-shaped plant with bases overlapping in a single row.
5. *Phormium tenax* 'TWISTED SISTER' exhibits stiff leaves that are folded folded lengthwise and twisted.
6. Cultural requirements for 'TWISTED SISTER' are full sun to partial shade, occasional to regular water, and well-draining soil.
7. *Phormium tenax* 'TWISTED SISTER' has produced no flowers to date.

8. *Phormium tenax* 'TWISTED SISTER' is hardy to USDA Zone 7.
9. *Phormium tenax* 'TWISTED SISTER' can be propagated using the methods of tissue culture or division.

BRIEF DESCRIPTION OF THE DRAWINGS

The accompanying color drawing labeled

FIG. 1 depicts a side view of the plant illustrating foliage and plant habit.

The drawing labeled FIG. 2 depicts a close up view of the foliage and leaf margins of 'TWISTED SISTER'.

Figure 1:
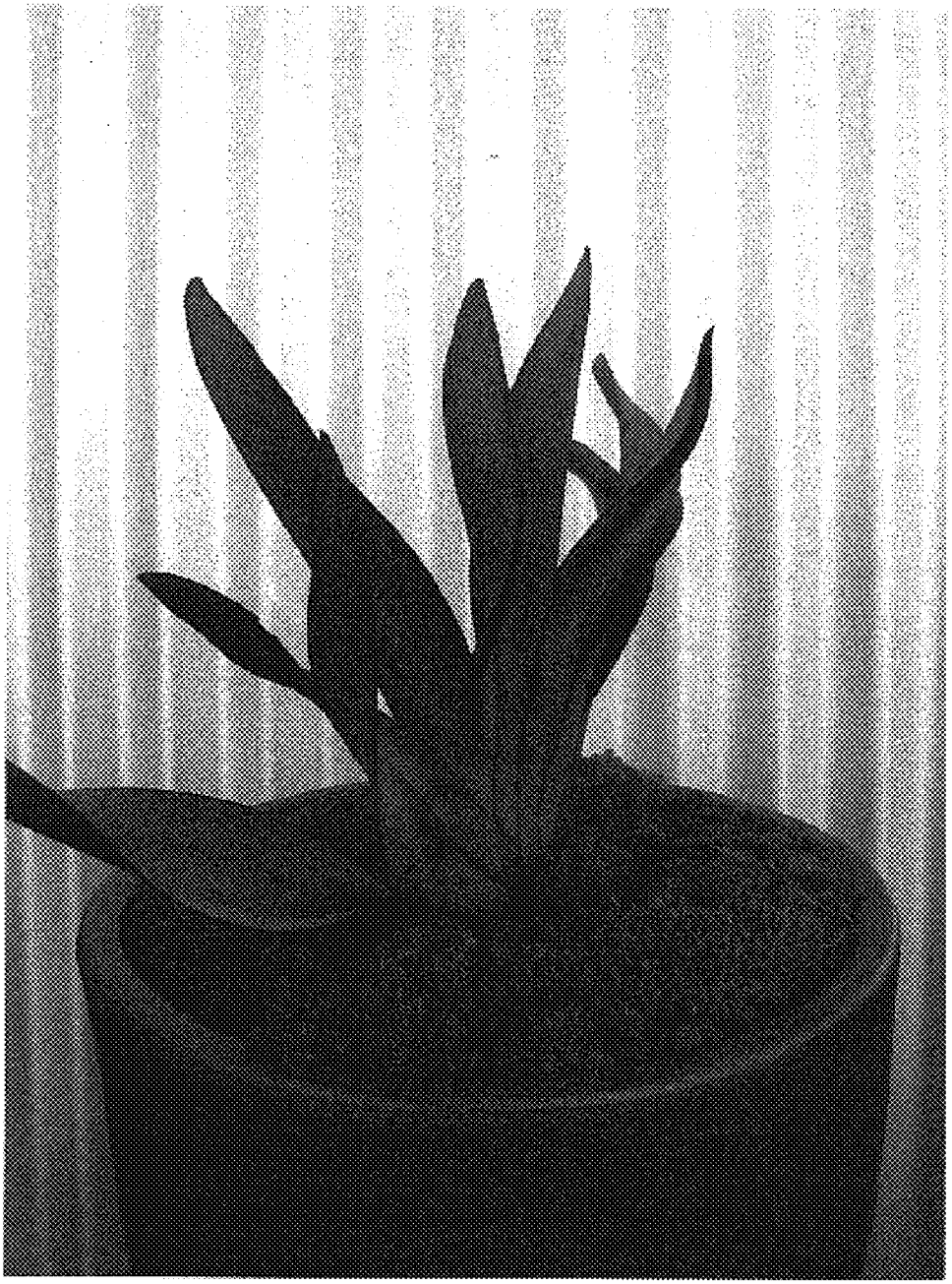
FIG. 1 and FIG. 2 illustrate the overall appearance of the new *Phormium* cultivar named 'TWISTED SISTER' showing the colors as true as it is reasonably possible to obtain in colored reproductions of this type. Colors in the drawings may differ from the color values cited in the detailed botanical description, which accurately describes the actual colors of the new variety 'TWISTED SISTER'. Both drawings were made in Auckland, New Zealand of an individual container plant grown in full sun and approximately two years old.
Figure 2:
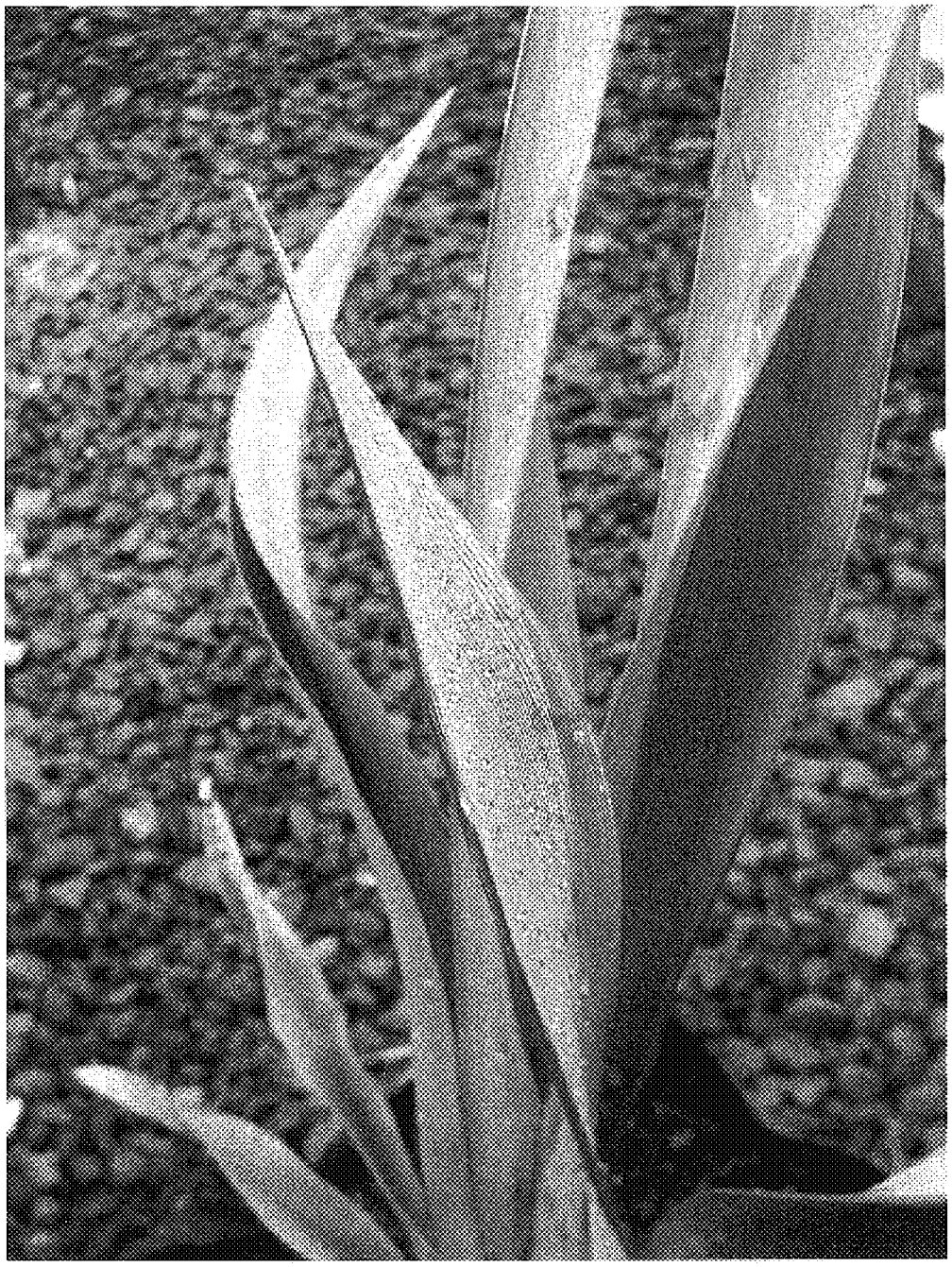

The drawings were made using conventional techniques and although colors may appear different from actual colors due to light reflectance they are as accurate as possible by conventional photography.

DETAILED BOTANICAL DESCRIPTION

The following is a detailed description of the new *Phormium* plant named 'TWISTED SISTER'. Data was collected in Arroyo Grande Calif. from 18-month-old plants growing in full sun out-of-doors in 1-liter commercial containers. The color determinations are in accordance with the 2001 edition of The Royal Horticultural Society Colour Chart, of London, England, except where general color terms of ordinary dictionary significance are used. The growing requirements are similar to other *Phormium*.

Botanical classification: *Phormium tenax* 'TWISTED SISTER'.
Genus: *Phormium*.
Species: *tenax*.
Denomination: 'TWISTED SISTER'.
Common name: New Zealand flax.
Plant type: Perennial.
Commercial classification: Evergreen shrub.
Commercial container size: 1-liter.
Plant use: Recommended for use in the landscape, or for use as a container plant.
Cultural requirements: Cultural requirements are full sun to partial shade, occasional to regular water, and well-draining loam soil.
Parentage: *Phormium tenax* 'TWISTED SISTER' was discovered as a naturally occurring individual whole plant mutation from an individual plant of *Phormium tenax*, (unpatented) within a commercial crop of *Phormium tenax*.
Disease and pest susceptibility or resistance: There is no disease or pest resistance known to the inventor.
Plant description:
- *Bloom period.*—No flowers have been produced to date.
- *Plant habit.*—Upright clumping.
- *Plant size.*—Small overall size.
- *Root system.*—Fibrous and fleshy.
- *Plant vigor.*—Low to moderate vigor.
- *Plant shape.*—Fan-shaped.
- *Plant height.*—41 cm. in height.
- *Plant width.*—43 cm. in width.
- *Plant hardiness.*—USDA Zone 7.
- *Plant propagation.*—Tissue culture and division.
- *Time to develop roots.*—2 months by method of tissue culture.
- *Crop time.*—From 18 to 24 months from a weaned microplant.

Foliage:
- *Branching pattern.*—Dense basal rosette formed in a single or flat plane.
- *Foliage type.*—Evergreen.
- *Quantity of leaves.*—Range of 9 to 11 leaves.
- *Leaf arrangement.*—Equitant.
- *Leaf shape.*—Gladiate.
- *Leaf division.*—Simple.
- *Leaf attachment.*—Sessile; Basally sheathing.
- *Leaf apex.*—Broadly acute.
- *Leaf base.*—Truncate.
- *Leaf margin.*—Entire, width 1 mm to 2 mm.
- *Leaf margin color.*—172A.
- *Leaf form.*—Twisting.
- *Leaf blade color* (*ventral surface*).—191A.
- *Leaf blade color* (*dorsal surface*).—189A.
- *Leaf blade surface* (*ventral surface*).—Minutely furrowed.
- *Leaf blade surface* (*dorsal surface*).—Minutely furrowed.
- *Leaf pubescence* (*ventral and dorsal surfaces*).—None observed.
- *Venation pattern.*—Inconspicuous parallel vein pattern.
- *Vein color* (*dorsal surface*).—189A.
- *Vein color* (*ventral surface*).—191A.
- *Leaf width.*—4 cm. in width.
- *Leaf length.*—Ranges from 24 cm. to 40 cm. in length.
- *Leaf fragrance.*—No fragrance observed.
- *Other significant leaf traits.*—Folded lengthwise and keeled on dorsal surface.
- *Keel width.*—1.50 mm, in width.
- *Keel color.*—175A.

Flower: 'TWISTED SISTER' has produced no flowers to date.

It is claimed:

1. A new and distinct cultivar of *Phormium* plant named 'TWISTED SISTER' as described and illustrated herein.

* * * * *